(12) United States Patent  
Gillis et al.

(10) Patent No.: US 6,368,315 B1
(45) Date of Patent: Apr. 9, 2002

(54) COMPOSITE DRUG DELIVERY CATHETER

(75) Inventors: Edward M. Gillis, Cupertino; Felix Theeuwes, Los Altos Hills, both of CA (US)

(73) Assignee: Durect Corporation, Cupertino, CA (US)

( * ) Notice: Subject to any disclaimer, the term of this patent is extended or adjusted under 35 U.S.C. 154(b) by 0 days.

(21) Appl. No.: 09/339,465

(22) Filed: Jun. 23, 1999

(51) Int. Cl.⁷ .............................................. A61M 25/00
(52) U.S. Cl. ..................................................... 604/523
(58) Field of Search ........................... 604/264, 96, 71, 604/101, 523, 524, 525, 526, 527, 528, 529, 530, 532, 533, 534, 535; 606/191–194

(56) References Cited

U.S. PATENT DOCUMENTS

| | | | |
|---|---|---|---|
| 4,464,176 A | 8/1984 | Wijayarathna | 604/164 |
| 4,739,768 A | 4/1988 | Engelson | 128/658 |
| 4,917,670 A | 4/1990 | Hurley et al. | 604/51 |
| 4,968,306 A | 11/1990 | Huss et al. | 604/264 |
| 5,100,379 A | 3/1992 | Wendell | 604/5 |
| 5,242,396 A | 9/1993 | Evard | |
| 5,308,342 A | 5/1994 | Sepetka et al. | 604/282 |
| 5,344,412 A | 9/1994 | Wendell et al. | 604/280 |
| 5,364,357 A | 11/1994 | Aase | 604/96 |
| 5,380,276 A | 1/1995 | Miller et al. | 604/28 |
| 5,425,723 A | 6/1995 | Wang | 604/280 |
| 5,462,523 A | 10/1995 | Samson et al. | 604/30 |
| 5,480,380 A | 1/1996 | Martin | 604/43 |
| 5,523,092 A | 6/1996 | Hanson et al. | 424/423 |
| 5,554,114 A | 9/1996 | Wallace et al. | 604/53 |
| 5,569,197 A | 10/1996 | Helmus et al. | 604/96 |
| 5,571,093 A | 11/1996 | Cruz et al. | 604/270 |
| 5,601,539 A | 2/1997 | Corson, Jr. | 604/282 |
| 5,643,228 A | 7/1997 | Schucart et al. | 604/264 |
| 5,676,659 A | 10/1997 | McGurk | 604/282 |
| 5,702,372 A | 12/1997 | Nelson | 604/264 |
| 5,718,678 A | 2/1998 | Fleming, III | 604/43 |
| 5,759,191 A | 6/1998 | Barbere | 606/194 |
| 5,769,814 A | 6/1998 | Wijay | 604/96 |
| 5,782,797 A | 7/1998 | Schweich, Jr. et al. | |
| 5,792,124 A | 8/1998 | Horrigan et al. | 604/282 |
| 5,795,340 A | 8/1998 | Lang | 604/283 |
| 5,797,869 A | 8/1998 | Martin et al. | 604/43 |
| 5,800,392 A | 9/1998 | Racchini | 604/96 |
| 5,810,789 A | 9/1998 | Powers et al. | 604/280 |
| 5,820,610 A | 10/1998 | Baudino | 604/280 |
| 5,827,225 A | 10/1998 | MaSchwab | 604/96 |
| 5,827,242 A | 10/1998 | Folmer et al. | 604/282 |
| 5,843,050 A | 12/1998 | Jones et al. | 604/280 |
| 5,851,203 A | 12/1998 | van Muiden | 604/282 |

FOREIGN PATENT DOCUMENTS

| | | |
|---|---|---|
| EP | 0 102 685 | 3/1984 |
| WO | WO 92/00113 | 1/1992 |
| WO | WO 96/15819 | 5/1996 |

Primary Examiner—Manuel Mendez
(74) Attorney, Agent, or Firm—Bozicevic Field and Francis LLP; Carol L. Francis

(57) ABSTRACT

The present invention features a composite catheter comprising an elongate outer member and an elongate inner member positioned within the outer member so that the inner and outer members define an interstitial space. The outer member has a size and other characteristics that facilitate handling and implantation of the composite catheter, while the inner diameter of the inner member has the size and other characteristics suitable for delivery of a drug through a lumen of the inner member. The interstitial space imparts flexibility to the composite catheter by, for example, removing material from the cross-sectional area that would otherwise provide additional stiffness to the catheter, and/or by accommodating movement of the outer member relative to the inner member.

43 Claims, 7 Drawing Sheets

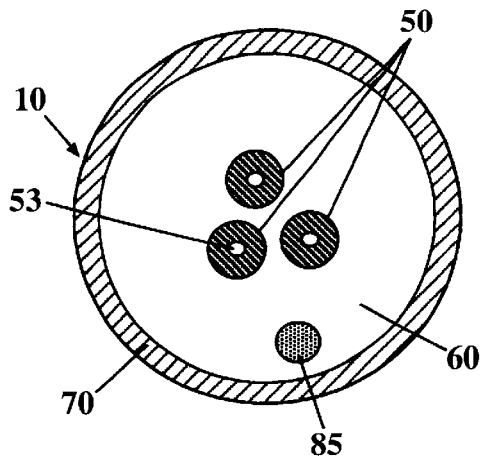
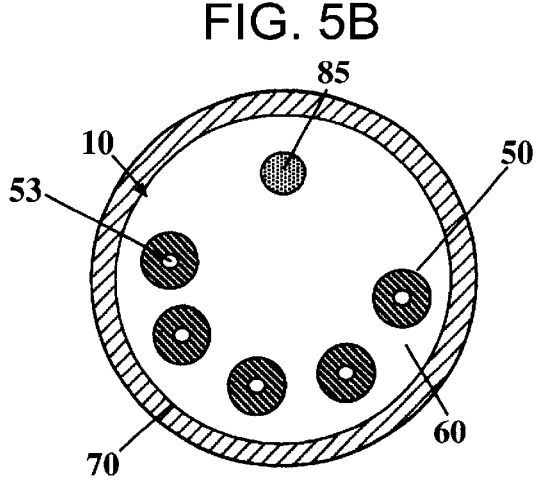
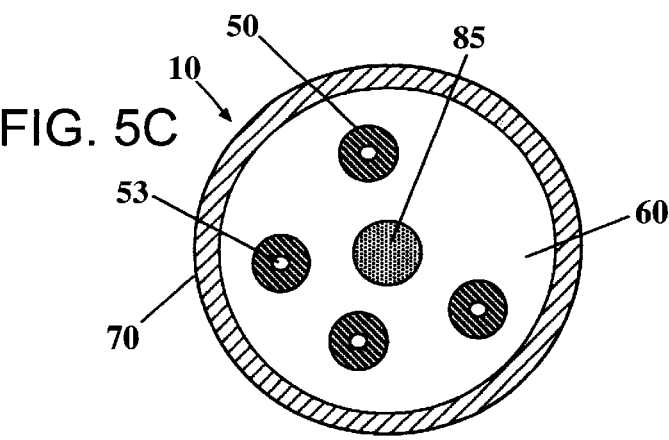
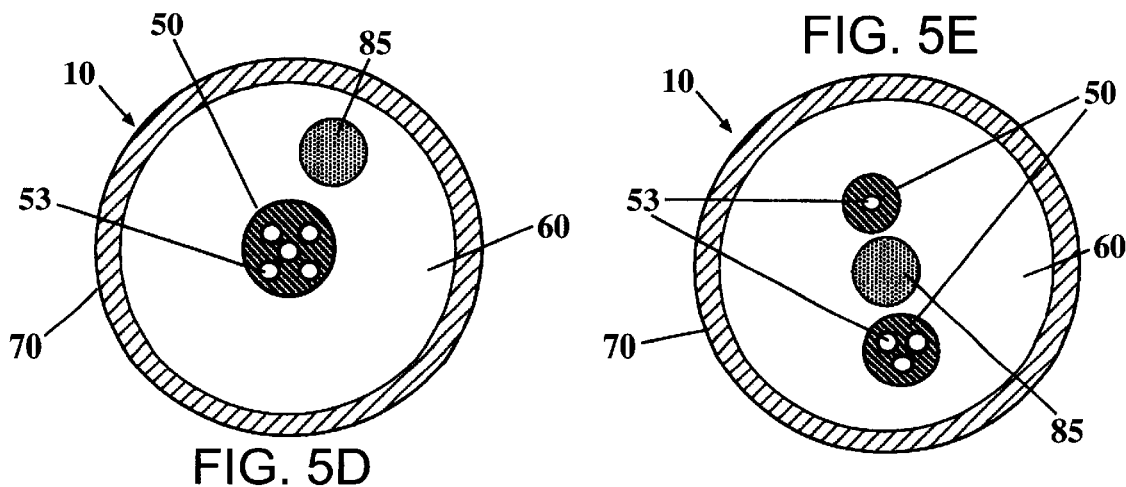

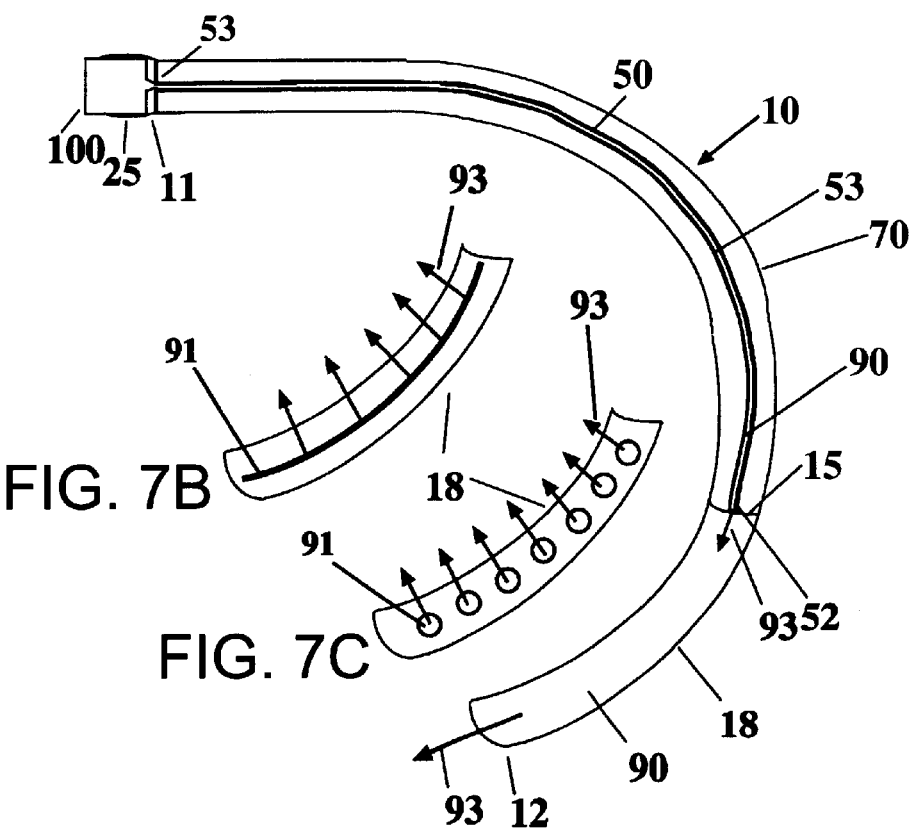
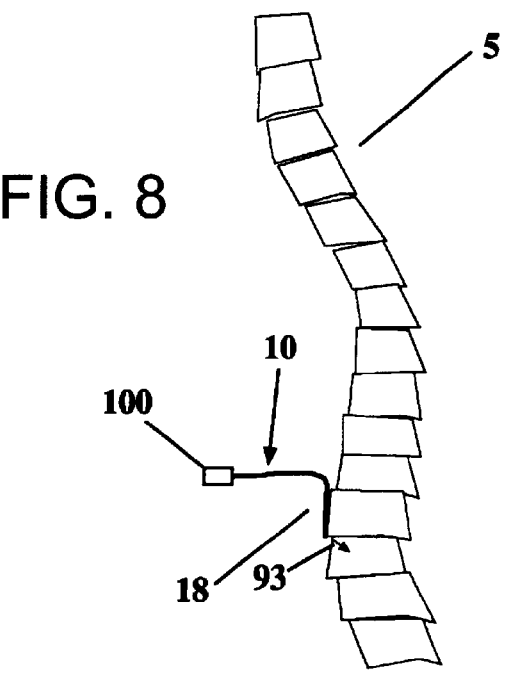

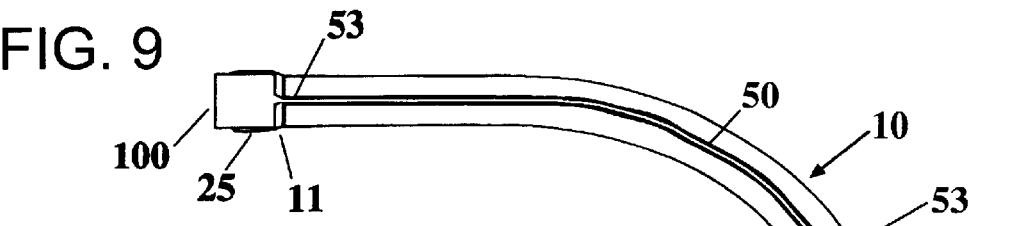
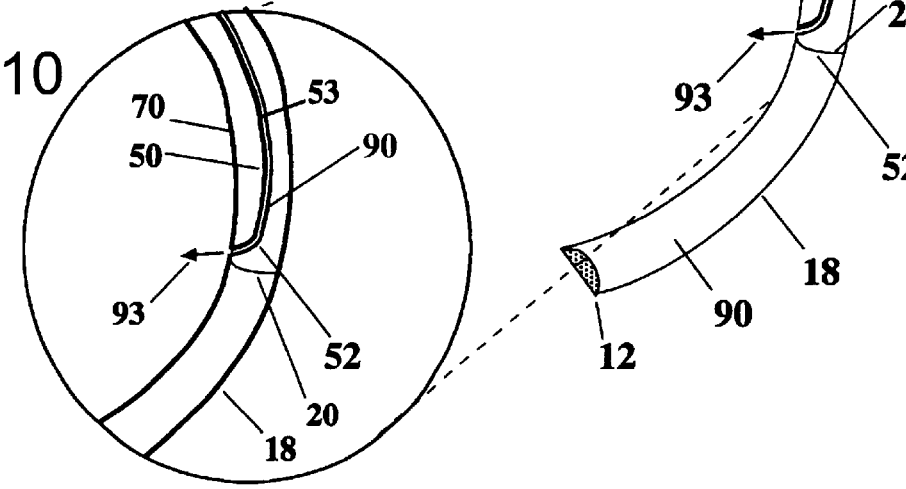
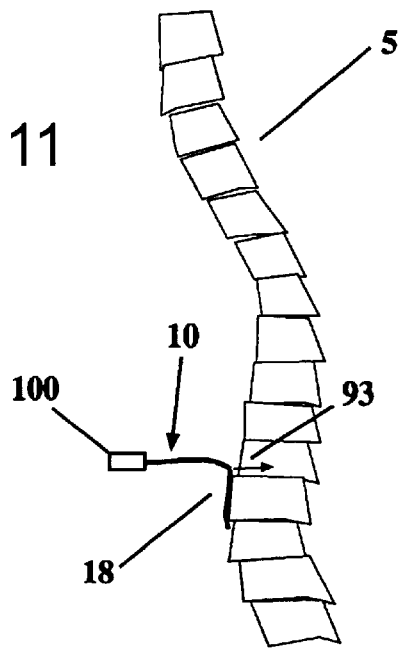

COMPOSITE DRUG DELIVERY CATHETER

FIELD OF THE INVENTION

This invention relates generally to catheters for use in delivery of drug, particularly in the context of site-specific drug delivery.

BACKGROUND OF THE INVENTION

Delivery of drug to a specific treatment site represents a substantial challenge in the design of drug delivery systems. Site-specific drug delivery can be particularly challenging when the drug is to be delivered long-term (e.g., several hours to several days, weeks, or months). One approach to accomplish site-specific drug delivery involves the use of a catheter, which can be positioned at a treatment site to facilitate localized delivery of drug from a drug reservoir that may be some distance from the treatment site. Long-term drug delivery requires that such catheters be biocompatible, drug non-reactive, impermeable, and flexible (e.g., not sharp or easily breakable while implanted in the body).

The combination of required characteristics of drug delivery catheters limits the materials available for their design. For example, while a variety of biocompatible materials have sufficient flexibility, these materials may not have the required impermeability and drug non-reactive characteristics. Similarly, while many materials may be both drug non-reactive and impermeable, they may not be sufficiently biocompatible and flexible.

The problem is further complicated where it is desirable to deliver drug in relatively small amounts, and thus requires a small drug delivery lumen. Catheters having a small inner lumen for drug delivery are often extremely difficult to handle due to, for example, their fragility and their small outer diameters. Adapting a catheter having a larger outer diameter to have a smaller inner lumen can provide a catheter that is handleable, but too stiff for implantation through tortuous bends in the implantation pathway that leads to the treatment site.

There is thus a need in the field for a drug delivery catheter that is biocompatible, flexible, handleable (even when designed for delivery of microquantities of drug), and sufficiently impermeable and drug non-reactive. The present invention addresses these problems.

SUMMARY OF THE INVENTION

The present invention features a composite catheter comprising an elongate outer member and an elongate inner member positioned within the outer member so that the inner and outer members define an interstitial space. The outer member has a size and other characteristics that facilitate handling and implantation of the composite catheter, while the inner diameter of the inner member has the size and other characteristics suitable for delivery of a drug through a lumen of the inner member. The interstitial space imparts flexibility to the composite catheter by, for example, removing material from the cross-sectional area that would otherwise provide additional stiffness to the catheter, and/or by accommodating movement of the outer member relative to the inner member.

In one aspect the invention features a catheter comprising an elongate outer member and an elongate inner member, where the inner member is positioned within a lumen defined by the outer member so as to define an interstitial space between an outer wall of the inner member and an inner wall of the outer member, and where a lumen defined by the inner member is suitable for delivery of drug at a low volume rate. In specific embodiments the catheter further comprises a support member positioned within the interstitial space.

In one embodiment, the catheter of the invention comprises a flexible distal portion. The flexible distal portion can be provided as an extension of a distal end of the outer member beyond the inner member distal end, or as an additional component attached to the distal end of the catheter. The flexible distal portion is flexible relative to a portion of the catheter comprising the outer member and the inner member.

In specific embodiments, the distal extension is substantially hollow, and the inner member lumen and a lumen defined by the flexible distal portion form a drug delivery conduit. In other specific embodiments, the drug delivery outlet is defined by an opening at a distal end of the flexible distal portion. In still other specific embodiments, the drug delivery outlet is defined in a sidewall of the flexible distal portion, or the inner member lumen terminates in a drug delivery outlet at a sidewall of the catheter proximal to the flexible distal portion.

In another aspect the invention features a drug delivery system comprising a drug delivery device and a composite catheter of the invention.

In another aspect the invention features a method for low volume rate delivery of a drug to a treatment site in a subject comprising the steps of: 1) implanting a catheter of the invention into a subject to provide a drug delivery pathway from a proximal end of the catheter, through a lumen defined by a catheter inner member to a distal end of the catheter, and out a drug delivery outlet positioned at a treatment site in a subject; and 2) introducing a drug into the inner lumen of the catheter to deliver drug to the treatment site in the subject.

A primary object of the invention is to provide a catheter useful in accurate and reliable delivery of very small volume of a drug, e.g., microliter quantities of a liquid or semisolid drug formulation, which catheter is biocompatible, flexible, and readily handleable to facilitate implantation.

Another object of the invention is to provide a catheter that can be used with a variety of drug delivery systems to accomplish site-specific drug delivery.

It is another object of the invention to provide a catheter that is suitable for delivery of drug to a distal treatment site within a subject, particularly sites that are highly sensitive or fragile (e.g., the spinal cord).

An important advantage of the invention is that the interstitial space defined by the inner wall of the outer member and the outer wall of the inner member accommodates movement of the outer and inner members relative to one another, e.g., in a plane perpendicular to a sidewall of the catheter, and further can make the catheter less stiff by removing material from the catheter cross-sectional area. Furthermore, the interstitial space can be designed to provide for varying degrees of flexibility of the catheter, e.g., by varying the dimensions of the space (e.g., the distance between the outer member inner wall and the inner member outer wall). The interstitial space can also be designed to accommodate other desirable catheter elements. For example, the space can be designed to accommodate one or more support members, which support members can enhance the tensile strength or compression strength of the composite catheter. In addition or alternatively, desirable characteristics can be imparted to the catheter by filling the interstitial space with a gas, liquid, semi-solid, or polymer (including cross-linked polymers) that is under substantially constant or regulatable pressure, and that optionally comprise antimicrobial (e.g., bacteriostatic or bactericidal) agents.

Another important advantage of the invention is that the composite catheter facilitates delivery of extremely small volumes of drug (e.g., submicroliter volumes), yet is easily handled, e.g., by a clinician during implantation. This advantage of the catheter is provided by the combined characteristics of the inner member, which provides the drug delivery conduit, and the outer member, which provides for the biocompatibility and ease of handling of the composite catheter. Furthermore, by facilitating delivery of small volumes of drug, the catheter reduces the economic costs as well as the risks associated with systemic dosing.

Another advantage of the invention is that the material used for the outer member need not be drug impermeable, since at most only the inner member need be substantially drug impermeable. Thus any available biocompatible and implantable grade material (e.g., silicone rubber) can be used for the outer member. Thus the catheter can take advantage of a wider range of biocompatible materials for the outer member than can conventional catheters in which the material of the outer catheter wall is in contact with the drug formulation to be delivered.

Another advantage of the invention is that the catheter inner member and the catheter outer member can have distinctly different characteristics in terms of, for example, relative flexibility, dimensions, biocompatibility, etc, which characteristics can be varied and selected according to any of a variety of factors, e.g., the drug to be delivered, the desired flow rate, the treatment site, etc. For example, the material of the outer member can be selected to provide for biocompatibility, size, flexibility, and other catheter characteristics important for implantation and retention in the subject without significant constraint imposed by the properties important for delivery of drugs, while the inner member of the composite catheter can be selected to provide the size, non-permeability to drug, non-reactivity to drug, and other characteristics optimal for delivery of drug without significant constraint imposed by biocompatibility, flexibility, and other characteristics important to handling and implantation in a subject. This combination allows for use of a wider variety of materials in the manufacture of the drug delivery conduit defined by the inner member since the outer member will protect the subject from the inner member material, e.g., the inner member may comprise materials that would be too sharp, stiff, or otherwise unsuitable for implanting in a subject. Similarly, the outer member can be provided in dimensions that facilitate ease of handling and implantation, while the inner member can be of relatively smaller dimensions, e.g., to define an extremely small inner lumen for delivery of drug at a relatively low volume rate. In addition, the use of the outer and inner member allows for more design flexibility, e.g., varying the inner and outer diameters to provide dimensions suitable for drug delivery and handleability, respectively; varying the materials for the outer member and the inner member to provide for biocompatibility and drug-impermeability, respectively; etc.

The invention is also advantageous in that the inner lumen of the inner member can be designed to provide a drug delivery conduit with a small lumen size to, for example, minimize start-up time, i.e., the time for delivery of drug from a drug reservoir of a drug release device, through the catheter, and to the treatment site.

Still another advantage of the invention is that the catheter can be designed to have an extremely floppy (flexible) distal portion that can serve as a means for anchoring the catheter at a treatment site, and can be cut to a desired length by the clinician to provide for tailoring the catheter to the present needs of the subject and/or treatment site. Furthermore, the drug delivery outlet can be positioned within a sidewall of the catheter to provide for delivery of drug at or about the anchoring point at a treatment site (e.g., at or about the point at which the floppy distal portion begins, see, e.g., FIGS. 9–11).

These and other objects, advantages and features of the present invention will become apparent to those skilled in the art upon reading this disclosure in combination with drawings wherein like numerals refer to like components throughout.

BRIEF DESCRIPTION OF THE DRAWINGS

FIGS. 5A, 5B, 5C, 5D, and 5E are cross-sectional views of exemplary composite catheters of the invention comprising a plurality of drug delivery conduits by comprising a plurality of inner members (FIGS. 5A, 5B, and 5C), an inner member defining a plurality of inner lumen (FIG. 5D), or both (FIG. 5E).

FIG. 7A is a partial cut-away view of an exemplary catheter of the invention, where the catheter comprises a floppy distal section and is positioned for use with a controlled drug release device.

FIGS. 7B and 7C are perspective views of exemplary, alternative embodiments of the catheter floppy distal end.

FIG. 8 illustrates the catheter and drug delivery device of FIG. 7 positioned for use in delivery of drug to the spinal cord of a subject.

FIG. 9 is a partial cut-away view of an exemplary catheter of the invention positioned for use with a controlled drug release device, where the catheter comprises a floppy distal section and a side exit through which drug is delivered.

FIG. 10 is an exploded view of the side exit of the catheter of FIG. 9.

FIG. 11 illustrates the catheter and controlled drug release device of FIG. 9 positioned for use in delivery of drug to the spinal cord of a subject.

DETAILED DESCRIPTION OF THE PREFERRED EMBODIMENTS

Figure 1:
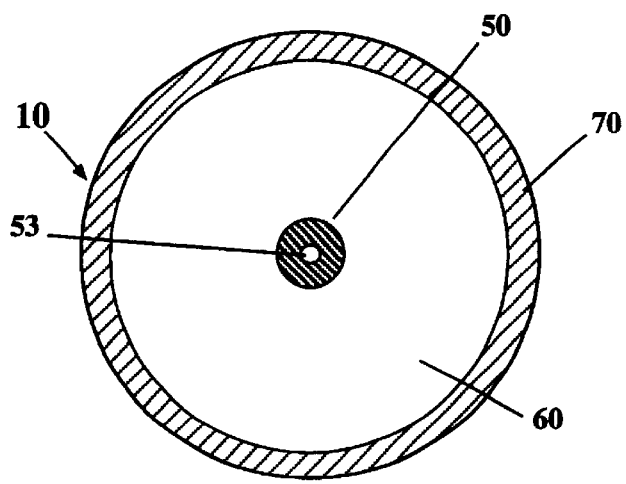
FIGS. 1 and 2 are cross-sectional and cut-away views, respectively, of an exemplary composite catheter of the invention.

Before the present composite catheter, method of drug delivery, and specific devices and formulations used in connection with such are described, it is to be understood that this invention is not limited to the particular embodiments described, as such methods, devices, and formulations may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural referents unless the context clearly dictates otherwise. Thus, for example, reference to "a formulation" includes mixtures of different formulations, and reference to "the method of delivery" includes reference to equivalent steps and methods known to those skilled in the art, and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the specific methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The term "low volume rate drug delivery" as used herein generally refers to delivery of a liquid or semisolid drug at a volume rate of from about 0.01 $\mu$l/day to about 200 $\mu$l/day, usually about 0.04 $\mu$l/day to about 20 $\mu$l/day, more usually about 0.1 $\mu$l/day to about 8.0 $\mu$l/day.

"Drug delivery device" as used herein is meant to encompass any device that comprises a drug reservoir and that facilitates movement of drug from the drug reservoir to a site external to the drug delivery device. "Drug delivery device" thus encompasses controlled drug release devices, as well as devices that release drug in an unpatterned (e.g., substantially unregulated) manner. Controlled drug release devices are particularly preferred for use with the catheter of the present invention.

"Controlled release" as used herein (e.g., in the context of "controlled drug release") is meant to encompass release of substance (e.g., a drug) at a selected or otherwise controllable rate, interval, and/or amount. "Controlled release" thus encompasses, but is not necessarily limited to, substantially continuous delivery, patterned delivery (e.g., intermittent delivery over a period of time that is interrupted by regular or irregular time intervals), and delivery of a bolus of a selected substance (e.g., as a pre-determined, discrete amount of a substance over a relatively short period of time (e.g., a few seconds or minutes).

The term "controlled drug release device" is meant to encompass any device that provides for controlled release of a drug or other desired substance, and that can be adapted for use with a catheter of the invention, e.g., a drug delivery device that provides for controlled release of drug through a catheter of the invention, and at a rate that is suitable to accomplish delivery of a therapeutically effective amount of drug to a treatment site according to the methods of the invention.

The term "treatment site" as used herein is meant to refer to a desired site for delivery of drug from a drug delivery device of the invention, and/or a site from which fluid sampling is desired, e.g., for diagnosis and/or prognosis. "Treatment site" is thus meant to include, although is not necessarily limited to, a subcutaneous, percutaneous, intravenous, intrathecal, intramuscular, intra-arterial, intravascular, intraperitoneal, intraspinal, epidural, intracranial, peritumoral, or intratumoral (i.e., within a cancerous growth) site within a subject, as well as sites within or near a selected organ or tissue (e.g., central nervous system (e.g., spinal fluid, brain, etc.), peripheral nervous system, kidney, liver, pancreas, heart (e.g., intrapericardial), lung, eye, ear (e.g., inner ear), lymph nodes, breast, prostate, ovaries, testicles, thyroid, spleen, etc.), digestive system (e.g., stomach, gastrointestinal tract, etc.), skeletal muscle, bone, urinary bladder, gall bladder, adrenal gland, adipose tissue, parathyroid gland, uterus, fallopian tube, skin, into a vessel associated with the circulatory system (e.g., artery, arteriole, blood vessel, vein, capillary bed, lymph vessel, particularly arteries that feed a selected organ or tissue)), a tumorous growth (e.g., cancerous tumor (e.g., solid tumor), cyst, etc.), at a site associated with a microbial infection (e.g., bacterial, viral, parasitic or fungal infection), or to an autologous or synthetic graft (e.g., a vascular graft).

The term "access site" or "implantation site" is used to refer to a site on or in a subject at which a catheter of the invention is introduced for implantation and positioning within the subject's body, e.g., for delivery of drug to a desired treatment site. For example, where a catheter is implanted in a subject for delivery of drug to the spinal cord, the access site or implantation site can be a subcutaneous site at which a proximal end of the catheter is substantially retained, and the treatment site is a position within or adjacent the spinal cord (treatment site) at which a distal end of the catheter is positioned for delivery of drug.

"Drug delivery system" as used herein is meant to refer to a combination of a catheter of the invention and a drug delivery device suitable for use in delivery of a drug to a treatment site, preferably a controlled drug release device.

The term "subject" is meant any subject, generally a mammal (e.g., human, canine, feline, equine, bovine, etc.), to which drug delivery is desired.

The term "impermeable" means that the material is sufficiently impermeable to environmental fluids as well as ingredients contained within the dispensing device such that the migration of such materials into or out of the device through the impermeable device is so low as to have substantially no adverse impact on the activity or function of the drug retained within the device during the delivery period.

The term "semipermeable" means that the material is selectively permeable, e.g., permeable to external fluids but substantially impermeable to other ingredients contained within the dispensing device and the environment of use.

The term "drug" as used herein is meant to encompass any substance suitable for delivery to a treatment site of a subject, which substances can include pharmaceutically active drugs, as well as biocompatible substances that do not exhibit a pharmaceutical activity in and of themselves, but that provide for a desired effect at a treatment site, e.g., to flush or irrigate a treatment site (e.g., saline).

"Pharmaceutically active drug," "therapeutic agent," "therapeutic drug," and the like are used interchangeably herein to refer to any chemical compound which, when provided to a subject (e.g., a mammal, preferably a human), facilitates a therapeutic effect. Such drugs may optionally be provided in combination with pharmaceutically acceptable carriers and/or other additional compositions such as antioxidants, stabilizing agents, permeation enhancers, etc.

In general, "drug" and the like are used to refer to any drug that is conventionally administered by parenteral injection (e.g., intravascularly, intramuscularly, subcutaneously, intrathecally, etc.). Drugs compatible for delivery using the devices and methods of the invention are discussed below, and are readily apparent to the ordinarily skilled artisan upon reading the disclosure provided herein.

The term "therapeutically effective amount" is meant an amount of a therapeutic agent, or a rate of delivery of a therapeutic agent, effective to facilitate a desired therapeutic effect. The precise desired therapeutic effect will vary according to the condition to be treated, the drug to be administered, and a variety of other factors that are appreciated by those of ordinary skill in the art. Determinations of precise dosages are routine and well within the skill in the art.

The term "treatment" is used here to cover any treatment of any disease or condition in a mammal, particularly a human, and includes: a) preventing a disease, condition, or symptom of a disease or condition from occurring in a subject which may be predisposed to the disease but has not yet been diagnosed as having it; b) inhibiting a disease, condition, or symptom of a disease or condition, e.g., arresting its development and/or delaying its onset or manifestation in the patient; and/or c) relieving a disease, condition, or symptom of a disease or condition, e.g., causing regression of the disease and/or its symptoms.

Composite Catheter

The present invention features a composite catheter comprising an elongate outer member, and an elongate inner member positioned within the outer member either concentrically (e.g., substantially coaxial) or non-concentrically (i.e., off-center) with respect to the outer member. The inner and outer members can be any suitable shape including, but not limited to, tubular, elliptical, cylindrical, etc., and may be either smooth on the composite catheter outer surface, or may comprise ridges (e.g., longitudinal, axial, or circumferential) or other surface variations as will be desirable for the specific applications for which the composite catheter is used. The inner and outer members are configured to define an interstitial space between an inner wall of the outer member and an outer wall of the inner member. The interstitial space imparts flexibility to the composite catheter by, for example, accommodating movement of the outer member relative to the inner member and/or by virtue of having less material in the catheter cross-sectional area. The interstitial space can also be designed to accommodate a support member, e.g., to provide tensile or compression support to the catheter.

In general, the inner member defines at least a portion of a drug delivery conduit, which conduit normally extends at least the length of the inner member and terminates in a drug delivery outlet. The outer member provides for the handleable and implantable characteristics of the catheter, while the inner member has an inner diameter optimized for delivery of a liquid or semisolid drug through the lumen of the inner member. The composite catheter can also be designed with a single outer member and one or a plurality of drug delivery conduits, which conduits can be defined by a single inner member or by a plurality of inner members and which can be designed for delivery of the same or different drugs to a treatment site. In use, the distal end of the catheter is positioned at a treatment site within the subject, while the proximal end of the catheter is associated with, for example, a drug delivery device. While the composite catheter of the invention is primarily intended for use in drug delivery, it may also be used in the course of other medical procedures (e.g., to facilitate sampling of fluid (e.g., spinal fluid) from the treatment site, etc.).

The inner member, the outer member, and various exemplary embodiments of the composite catheter will now be described in more detail.

Catheter Inner Member Materials and General Characteristics

As noted above, the catheter inner member defines at least a portion of the catheter drug delivery conduit, and in particular defines that portion of the catheter drug delivery conduit that is characterized by an inner diameter suitable for delivery of drug at a desired rate, e.g., low volume rate delivery, e.g., 0.01 μl/day to about 200 μl/day. In general, the inner diameter of the catheter inner member is from about 0.0002" (about 0.005 mm) to about 0.025" (about 0.6 mm), usually from about 0.0005" (about 0.013 mm) to about 0.015" (about 0.4 mm), generally from about 0.001" (about 0.025 mm) to about 0.010" (about 0.25 mm), and preferably from about 0.002" (about 0.05 mm) to about 0.006" (about 0.15 mm). The thickness of the inner member walls will vary with a variety of factors, such as the stiffness and permeability of the material selected, e.g., a metal-based material may have a very thin wall section (e.g., less than 0.001"), while a glass- or polymer-based material may have a thicker wall).

The catheter inner member is preferably produced from any of a variety of suitable drug impermeable materials. Preferably, drug impermeable materials suitable for use in production of the catheter inner member do not react in an unintended manner with the active agent formulation. Suitable materials for the catheter inner member can comprise a drug non-reactive polymer or a biocompatible metal or alloy. Exemplary materials from which the catheter inner member can be manufactured include, but are not necessarily limited to, polymers; metals; glasses; polyolefins (high density polyethylene (HDPE), low density polyethylene (LDPE), linear low density polyethylene (LLDPE), polypropylene (PP), and the like); nylons; polyethylene terephtholate; urethanes; PEBAX™; HYTREL™; TEFLON™; fluorenated polymers (e.g., polytetrafluoroethylene (PTFE), PFA); poly(methyl) methacrylate) (PMMA); polyvinylidine chloride; laminates of hydrophilic polymers and hydrophobic polymers, acrylonitrile, nickel titanium, superelastic nickel titanium, multilaminates or polymer, metals, and/or glass; and the like. In a particularly preferred embodiment, the inner member is manufactured from nickel titanium, particularly superelastic nickel titanium (NITINOL™).

Further specific exemplary polymers suitable for use in production of the catheter inner member include, but are not necessarily limited to, acrylonitrile polymers such as acrylonitrile-butadiene-styrene polymer, and the like; halogenated polymers such as polytetrafluoroethylene, polychlorotrifluoroethylene, copolymer tetrafluoroethylene and hexafluoropropylene; polyimide; polysulfone; polycarbonate; polyethylene; polypropylene; polyvinylchloride-acrylic copolymer; polycarbonate-acrylonitrile-butadiene-styrene; polystyrene; and the like. Further exemplary polymers are described in *Plastics Materials* 6th ed., May 1995, J. A. Brydson, Butterworth-Heinemann, publishers. Metallic materials suitable for use in production of the catheter inner member include stainless steel, titanium, platinum, tantalum, gold and their alloys; gold-plated ferrous alloys; platinum-plated titanium, stainless steel, tantalum, gold and their alloys as well as other ferrous alloys; cobalt-chromium alloys; and titanium nitride-coated stainless steel, titanium, platinum, tantalum, gold, and their alloys.

The catheter inner member can comprise additional materials or agents. For example, the inner member can comprise a coating on an internal wall to facilitate transport of drug through the inner lumen, or to impart other desirable characteristics to the catheter. The catheter can also comprise coatings that reduce the risk of infection, e.g., a silver coating, a coating or treatment with an antimicrobial agent (s), etc.

Catheter Outer Member Materials and General Characteristics

The catheter outer member is generally a substantially sheath-like structure comprising a proximal end, a distal end, and an outer member body. The catheter outer member can be positioned around, either concentrically or non-concentrically (i.e., off-center) relative to a catheter inner member (see, e.g., FIGS. 1, 2, and 5A–5C). The thickness of the outer member wall will vary depending on, for example, the material selected and the desired flexibility, permeability, etc. The dimensions of the outer member (e.g., inner diameter, outer diameter, thickness of the outer member wall etc.) can be substantially the same throughout the length of the catheter, or can be varied. For example, the outer member can be tapered at the distal end to dimensions similar to that of the inner member.

The outer diameter of the outer member, which generally defines the outer diameter of the composite catheter, is of a size that provides for ease of handling the composite catheter. In general, the diameter of the outer member is from about 0.01" (about 0.25 mm) to about 0.200" (about 5 mm), usually from about 0.020" (about 0.5 mm) to about 0.100" (about 2.5 mm), generally from about 0.025" to about 0.080", preferably from about 0.030" (about 0.75 mm) to about 0.060" (about 1.5 mm). In one embodiment, the outer member outer diameter is from about 0.040" to about 0.050".

The outer member is preferably made of a biocompatible material, more preferably an implantable grade biocompatible material. Exemplary materials suitable for the outer member include, but are not necessarily limited to, biocompatible polymers and/or elastomers. Suitable biocompatible polymers include, but are not necessarily limited to, materials such as, for example, polyethylene, homopolymers and copolymers of vinyl acetate such as ethylene vinyl acetate copolymer, polyvinylchlorides, homopolymers and copolymers of acrylates such as polymethylmethacrylate, polyethylmethacrylate, polymethacrylate, ethylene glycol dimethacrylate, ethylene dimethacrylate and hydroxymethyl methacrylate, polyurethanes, polyvinylpyrrolidone, 2-pyrrolidone, polyacrylonitrile butadiene, polycarbonates, polyamides, fluoropolymers such as polytetrafluoroethylene and polyvinyl fluoride, polystyrenes, homopolymers and copolymers of styrene acrylonitrile, cellulose acetate, homopolymers and copolymers of acrylonitrile butadiene styrene, polyvinylchloride, silicone rubber, polymethylpentene, polysulfones, polyesters, polyimides, polyisobutylene, polymethylstyrene and other similar compounds known to those skilled in the art. Suitable, biocompatible elastomers include, but are not necessarily limited to, biocompatible elastomers such as medical grade silicone rubbers, polyvinyl chloride elastomers, polyolefin homopolymeric and copolymeric elastomers, urethane-based elastomers, and natural rubber or other synthetic rubbers, fluorenated polymers (e.g., PTFE), and the like. It should be understood that these possible biocompatible materials are included above for exemplary purposes and should not be construed as limiting.

The outer member can be made of a material that is relatively softer than the material of the inner member, e.g., the outer member can have a relatively lower flexural modulus, and the inner member can have a relatively higher flexural modulus. For example, the outer 3,515 kg/cm$^2$), while the inner member has a flexural modulus within the range from about 50,000 to 300,000 psi (3,515 to 21,100 kg/cm$^2$). Examples of materials with lower flexural modulus suitable for the outer member include urethanes, PVC, low density polyethylenes, and silicone rubbers. It should be noted that one intent of the invention is to design a more flexible outer member relative to the inner member. Since flexibility is imparted by the product of member wall thickness times the flex modulus of the material of the wall, these two parameters can be varied to provide an outer member having a desired flexibility. In general, a low flex modulus is desired. However a relatively higher flex modulus times a thin wall thickness can also results in such an overall flexible outer member.

The catheter outer member can comprise additional materials or agents. For example, the outer member can comprise a coating or be treated (e.g., on an external wall) to facilitate implantation of the catheter within the subject, to reduce the risk of infection (e.g., antimicrobial agents), and/or to impart other desirable characteristics to the catheter.

Exemplary Specific Embodiments of the Composite Catheter of the Invention

Referring generally to one non-limiting embodiment of the catheter of the invention illustrated in FIG. 1, the catheter 10 of the invention comprises an inner member 50 and an outer member 70, where the inner member 50 is positioned within the outer member 70, i.e., inner member 50 is inside outer member 70. The inner wall of the outer member 70 and the outer wall of the inner member 50 define interstitial space 60 that extends the length of the catheter inner member 50.

The dimensions of the catheter 10 outer diameter (which is generally defined by the outer diameter of the outer member 70) is of a size that facilitates handling of the catheter during implantation, and can be of any diameter suitable for introduction into a wide range of implantation sites (e.g., arteries, capillaries, ducts of organs, etc.). The catheter outer diameter can be substantially the same throughout the entire length of the catheter, or can vary along the catheter's length (e.g., the catheter can be tapered or narrowed at any point along the catheter body, e.g., tapered at a distal end). The dimensions of the catheter and its components can be varied according to a variety of factors such as the treatment site with which the catheter is to be used, desired physical characteristics of the catheter, etc. For example, the outer member diameter and/or wall thickness can be greater over those portions of the catheter where increased relative stiffness is desired and less over those portions of the catheter where increased relative flexibility is desired.

In general, the drug delivery conduit 90 of the catheter 10 is defined by the inner member 50 inner lumen (see, e.g., FIG. 1), or a combination of the inner member 50 inner lumen and the inner lumen of a floppy distal portion of the outer member (see, e.g., FIG. 7A, in which the drug delivery pathway is extended beyond the inner member distal end by a portion of the outer member distal end). Where the drug delivery conduit is defined by a combination of the inner member lumen and a lumen of a distal extension, the lumen of the inner member can be the same or substantially smaller than the lumen of the distal extension of the outer member. The portion of the drug delivery conduit defined by the inner member 50 is of an inner diameter compatible with the desired delivery characteristics for the drug, e.g., delivery at a relatively low volume rate. As with the catheter outer diameter, the catheter inner diameter can be substantially the same throughout the entire length of the catheter, or can vary along the catheter's length. For example, the drug delivery conduit catheter can be tapered or narrowed at any point along the catheter body, e.g., tapered at a distal end, or can be widened at any point along the catheter body, e.g., widened over a distal portion of the catheter.

The interstitial space 60 defined by the inner and outer members enhances the flexibility of the composite catheter, e.g., by removing material from the cross-sectional area of the catheter (e.g., material that would otherwise impart some stiffness to the catheter shaft), and/or by accommodating movement of the inner and outer members relative to each other. The cross-sectional width of the catheter interstitial space (e.g., the distance from the outer member inner wall to the inner member outer wall) will vary with a variety of factors such as the degree of flexibility desired, the total desired outer diameter of the catheter, the thickness of the outer member wall, the thickness of the inner member wall, and the total outer diameter of the inner member. The desired width of the interstitial space can be varied to accommodate other catheter elements, such as a support member positioned within the interstitial space, radiopaque markers, etc. The interstitial space width can be substantially the same or varied over the length of the catheter.

In general, the elements of the composite catheter can be designed so that the catheter is sufficiently flexible to pass through any tortuous bends in the implantation pathway (e.g., intricate bends in a vessel or duct into which the catheter is implanted. Catheters of varying stiffness and/or flexibility can be produced by, for example, varying the materials used to produce the catheter components (e.g., by using materials having a relatively high or low flexural modulus), and/or by varying the material or elements within the interstitial space. For example, the interstitial space 60 can be substantially empty, or partially or substantially filled with materials that impart a selected flexibility. Alternatively or in addition, a support member (e.g., compression or tensile support member, e.g., a sheath or guidewire) may be provided either around the outside of the catheter body and/or positioned within the interstitial space. The use of such a support member(s) can allow for use of less stiff materials for all or a portion of the catheter body. Various embodiments of the support members are described below in more detail.

In general, the dimensions of the catheter (e.g., overall length, outer diameter, inner diameter, wall thickness, etc.) can be varied as required or desired, and will vary according to a variety of factors (e.g., the treatment site for delivery, the drug delivery device used in connection with the catheter, etc.). For example, the inner diameter of the drug delivery conduit 90 of catheter 10 can be equal to, or can be greater or less than, the diameter of an orifice from which drug flows from a drug reservoir of a drug delivery device that is to be used with the catheter. In one embodiment, the proximal end of the catheter can comprise an inner diameter that is equal to or greater than the diameter of the orifice of a drug release device to be used with the catheter, and then taper over its length to a relatively smaller inner diameter, e.g., to provide a drug delivery outlet at the distal end. In general, the inner and outer diameters of at least the proximal end of the catheter is preferably of a size sufficient to provide a leak-resistant or leak-proof drug flow path from a drug reservoir of the drug delivery device through the catheter drug delivery conduit. Where the controlled drug release system used in the drug delivery device dispenses drug by convection (as in e.g., peristaltic or osmotic drug delivery systems), the drug delivery device orifice size as well as the inner diameter of the catheter drug delivery conduit can be designed as described by Theeuwes (1975) *J. Pharm. Sci.* 64:1987–91. In general, the catheter has an overall length in the range from about 1 cm to about 200 cm, usually from about 5 cm to about 150 cm, normally 10 cm to about 50 cm, more usually from about 15 cm to about 40 cm.

The outer member 70 and inner member 50 can be made from the same materials or from different materials. The inner member 50 is preferably made from a material that allows for production of a small diameter lumen (e.g., a lumen of a diameter suitable for accomplishing low volume rate delivery of drug) and is preferably substantially impermeable to drug. The outer member 70 is made of a biocompatible material that preferably provides for long-term implantability in a subject (e.g., for a period of days to weeks to years).

In one preferred embodiment, the composite catheter of the invention is composed of a silicone outer member and a nickel titanium alloy inner member. The inner diameter of the inner member is about 0.003" to 0.006," and the outer diameter of the inner member is about 0.005" to about 0.012".

The outer member 70 and inner member(s) 50 can be associated in a variety of ways to provide the catheter 10 of the invention. For example, the inner and outer members may be joined by connecting walls 15 at the proximal 11 and/or distal 12 ends of the catheter 10, which walls can serve to substantially isolate the interstitial space from the external environment. Alternatively or in addition, the inner and outer members can be joined together at their ends by crimping, heat fusion, ultrasonic welding, radio frequency welding, heat bonding, solvent bonding, soldering, etc. The outer and inner members can be joined by a mechanical element, such as a press fit or locking element. Alternatively or in addition, the outer and inner members can be connected by an adhesive material, which may be placed within the interstitial space, minimally at the extreme proximal and distal ends of the inner member so as to hold the inner member in place within the outer member. Suitable adhesives include, but are not necessarily limited to, epoxy resins, ethylene vinyl acetate-based adhesives, polyurethane, cyanoacrylates, UV curable adhesives, RTV silicone adhesives, as well as other silicone-based adhesives, solvent bonding adhesive substances, polyisobutylene (PIB)-based adhesives, and the like. Additional suitable adhesives are well known in the art, see, e.g., *Handbook of Adhesive Technology,* A. Pizzi and K. L. Mittal, January 1994, Marchel Dekker, publisher.

Elements within the Interstitial Space

The interstitial space can comprise one or more elements to enhance or provide the catheter with desirable characteristics. In one embodiment, the interstitial space is filled or substantially filled with one or more of a liquid, semi-solid, polymer, cross-linked polymer, air or other gas (e.g., an inert gas), etc. Where the walls of the interstitial space 60 (i.e., the inner wall of outer member 70, the outer wall of inner member 50, and the connecting walls 15) are made of a substantially impermeable material, the interstitial space can be filled with gas or liquid, and permanently sealed so as to maintain a relatively constant pressure (e.g., at least greater than atmospheric pressure) in the interstitial space. Alternatively, the connecting wall at the catheter proximal end can be made of a relatively gas permeable material (e.g., a gas-permeable membrane), or the proximal connecting wall can define an opening through which gas or liquid can be introduced into the interstitial space. The catheter proximal end can then be permanently or intermittently connected to a source of gas or liquid (e.g., a pressurized gas or pressurized liquid source) so that the pressure within the interstitial space can be maintained at a desired level or regulated. The pressure of the gas or liquid in the interstitial space 60 can provide a means to regulate the stiffness of the otherwise very flexible catheter. For example, where it may be desirable to increase the catheter's overall stiffness, e.g., while pushing the catheter through a vessel during implantation, the pressure of the gas in the interstitial space can be increased to make the catheter more stiff or can be decreased to render the catheter more flexible upon reaching a tortuous bend in the implantation pathway. This embodiment of the invention can also be adapted to substitute a semi-solid, liquid, or liquid-gas mixture for the gas in the interstitial space as described above.

Support Members

In another embodiment, the interstitial space comprises a support member. The support member can provide the catheter with tensile strength (e.g., to absorb longitudinal stress on the catheter) or with compression strength (e.g., to facilitate pushing of the catheter to an implantation site) and can facilitate implantation of the catheter. As used herein, support members that impart tensile strength to the catheter are referred to as "tensile support members," while support members that impart compression strength to the catheter are referred to as "compression support members." The characteristic(s) conferred on the catheter by the support member can be varied by, for example, varying the materials from which the support member is made, varying the structure of the support member (e.g., a coil-like structure to provide compression strength, or a braid-like structure to provide tensile strength), varying the thickness of the support member, varying the association of the support member with an element of the catheter (e.g., attaching the support member to the inner wall of the outer member, the outer wall of the inner member, or both), and/or varying the position of the support member (e.g., proximity of the support member to the outer member or inner member walls).

Figure 3:
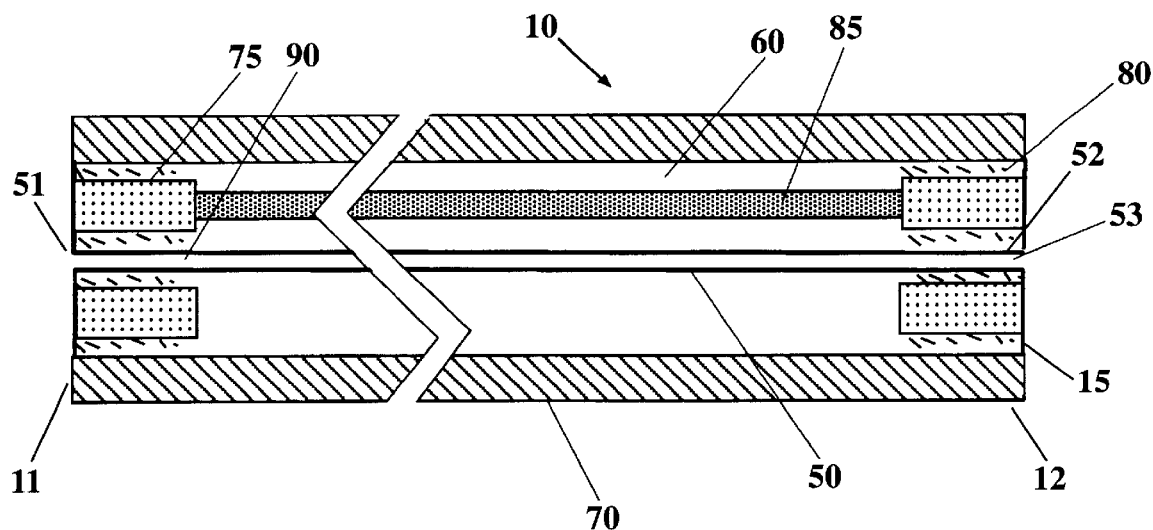
FIG. 3 is a cut-away view showing a composite catheter having a support member incorporated into the catheter interstitial space.

The support member can be provided in a variety of configurations (e.g., geometrical shapes, e.g., substantially straight or in a pre-set shape to give all or a portion of the catheter a desired configuration to facilitate access to a specific region) and a variety of dimensions (e.g., length, diameter, etc.) as suitable to provide the desired tensile or compression strength. For example as shown in FIG. 3, the support member 85 can extend through the interstitial space 60 for substantially the entire length of the inner member (e.g., from the inner member proximal end 11 to at least the inner member distal end 52) and, in other embodiments, may extend the entire length of the catheter, e.g., the entire length of both the inner and outer members.

The support member diameter can be substantially the same throughout its length, or may vary, e.g., the support member diameter can be greater over those portions of the catheter where increased relative stiffness is desired and less over those portions of the catheter, where increased relative flexibility is desired. The dimensions and/or configuration of the support member can be varied with the dimensions of the inner member, the outer member, or both. For example, where the inner and/or outer member diameter(s) taper or are otherwise altered to provide a relatively floppy portion of the catheter (e.g., a floppy distal end), the support member diameter can be relatively smaller at the portion of the catheter where flexibility is desired.

Figure 4:
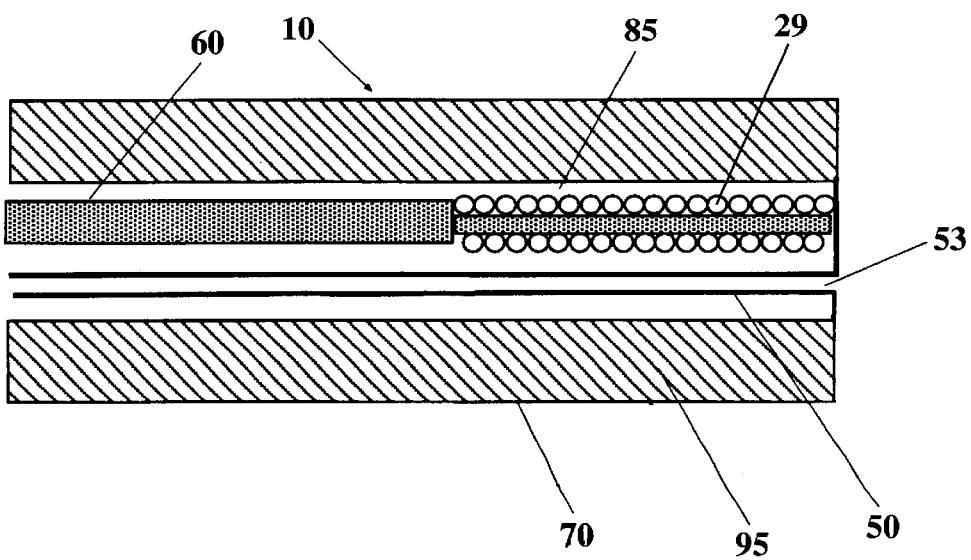
FIG. 4 is a cut-away view of a catheter comprising a tapered support member comprising a braid around a portion of smaller diameter.

In some embodiments it may be desirable to use a support member having a combination of structural configurations. For example, as shown in FIG. 4, the support member 85 can be associated with a coil or braid 29 positioned around the outer diameter of the support member 85 over the region of smaller support member diameter, e.g., a Teflon-coated stainless steel wire of from about 0.012" to 0.018".

Materials for support members can be selected according to the desired design, e.g., to provide for tensile strength or for compression strength. Exemplary materials for use in the support member include, but are not necessarily limited to, metals (e.g., stainless steel wire, parylene-coated or Teflon-coated stainless steel), metal alloys (e.g., nickel titanium (NITINOL™)), polymers (e.g., particularly polymers of relatively high modulus, e.g., carbon fiber,) and the like.

Compression Support Members

Where the support member is a compression support member, the support member can be substantially permanently positioned within the catheter interstitial space, or can be provided as a removable member, e.g., the support member can be withdrawn from the catheter after implanting. Where the support member is removable from the catheter, it may be preferable to enhance the slideability of the surfaces of the support member, outer member inner wall, and inner member outer wall, e.g., by Teflon or parylene coating of the support member, etc. Where the compression support member is substantially permanently positioned in the interstitial space, the support member 85 can be held in place by adhesive 80 at the proximal and/or distal ends of the support member 85. Exemplary solid compression support member materials include, but are not necessarily limited to, carbon fiber, metal, polycarbonate, plexiglass, etc.

A preferred compression support member is a wire-like element, preferably teflon-coated stainless steel, having a diameter within the range of from about 0.006" to about 0.020" (see, e.g., FIG. 3). The dimensions of the support member can be substantially the same throughout its length or may vary, e.g., the support member diameter can be greater over those portions of the catheter where increased relative stiffness is desired and less over those portions of the catheter where increased relative flexibility is desired.

Tensile Support Member

Where the support member is a tensile support member, the support member is generally permanently positioned within the interstitial space. The tensile support member can be attached to the catheter at its proximal and distal ends, or at any of at least two points along its length. Exemplary tensile support members include, but are not necessarily limited to, a wire, a braid (e.g., a braid that is positioned on the inner wall of the outer member, and which may form a spiral along the outer member inner wall for at least a portion of the length of the catheter that encloses the inner member), an inner liner layer (e.g., that is positioned adjacent the inner wall of at least a portion of the outer member, or positioned in the interstitial space between the outer member inner wall and the inner member outer wall), a sheath (e.g., surrounding the outer wall of the inner member) and other tensile support-providing elements. The support member is held in place within the catheter interstitial space by any suitable means, e.g., adhesive, insertion and retention within a portion of the outer member wall (e.g., through use of a mechanical press fit or nut and bolt action), etc. The support member can be molded in an outer wall of one or more members. The inner member may be longer than the support member to avoid tensile load.

Exemplary Variations of the Composite Catheter of the Invention

A number of variations on this basic catheter design are contemplated by the present invention. For example, although a substantially cylindrical catheter shape is described herein as exemplary, the catheter can be formed into any of a variety of dimensions and geometries, which are selected to be most suitable for the intended use of the drug delivery device (e.g., the desired treatment site, the amount of drug to be delivered, the drug delivery device to be used in conjunction with the catheter, the desired means of attachment of the catheter to the drug delivery device to facilitate flow of drug from the drug delivery device to the catheter, etc.). The catheter may comprise a single drug outlet at the distal end for delivery of drug at or near a treatment site, or may comprise a plurality of such drug outlets (e.g., in the form of side holes along a portion of the distal end of the catheter that communicate with a drug delivery conduit defined by the inner diameter of the inner member, the outer member, or both). The catheter may comprise a single drug delivery conduit (e.g., defined by a single inner member), or may comprise a plurality of drug delivery conduits (e.g., defined by one or more inner members positioned within a single outer member).

Figure 2:
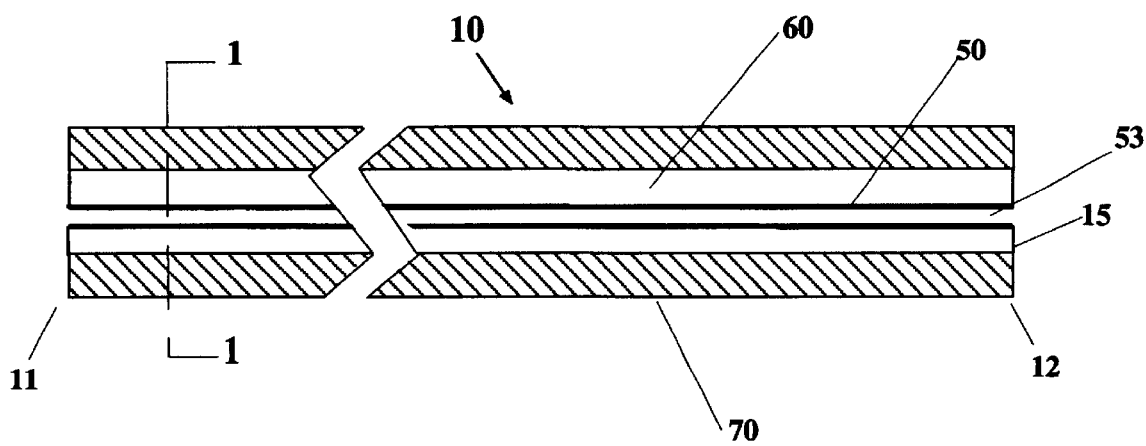

The catheter of the invention can also be modified by varying the relative lengths of the inner and outer members. For example, FIGS. 2 and 3 depict a catheter having an inner member 50 and an outer member 70 that are of substantially equal lengths, and that are positioned so that the inner member is substantially completely enclosed within the inner walls of the outer member (i.e., the proximal and distal ends of the inner and outer members terminate substantially within a single plane perpendicular to the proximal and distal ends). However, the invention also contemplates catheters comprising inner and outer members that terminate in different perpendicular planes at the catheter proximal end, the catheter distal end, or both. For example, in one embodiment the distal end of the catheter outer member extends distally beyond the distal end of the catheter inner member.

The catheter 10 of the invention can be further modified by providing a radiopaque marker 75 at one or more locations along its length (see, e.g., FIG. 3). In one embodiment, radiopaque markers are positioned within the catheter interstitial space 60 at or near the catheter distal end. As exemplified in FIG. 3, a radiopaque marker 75 can be provided in connection with a support member 85 (e.g., positioned at the distal end of a support member) and can further provide a surface for placement of adhesive 80 to hold the support member 85 the radiopaque marker 75, and the inner member 50 in place within the outer member 70. Suitable radiopaque markers can comprise metal rings (e.g., platinum, palladium, gold, etc.) as exemplified in FIG. 3, or can be provided by impregnating or coating all or a portion of the catheter body (e.g., the body of the outer member or inner member) with appropriate radiopaque dyes or other radiopaque materials. The provision of radiopaque markers is well known in the art.

In other variations contemplated by the invention, the distal end of the catheter is shaped so as to allow for smooth passage through such tortuous bends. For example, the distal end of the catheter can be provided as a rounded tip that allows for the catheter to move smoothly around such bends (e.g., where a square-ended catheter tip might catch on the sidewalls of a vessel or duct, thus frustrating implantation or placing the subject at risk of injury). In other variations, the distal end of the catheter optionally ends in a one-way valve such as a duck bill valve to prevent retrograde flow into the catheter, with external pressure at that distal end. Alternatively or in addition, the distal end may comprise a porous plug that serves as a filter element preventing particulate matter (including bacteria) from exiting from the catheter and into the treatment site.

The catheter can also be provided as a multi-lumen catheter, e.g., a composite catheter comprising an outer member with a plurality of inner members, where at least one inner member lumen serves as a drug delivery conduit (see, e.g., FIGS. 5A, 5B, and 5C); a composite catheter comprising an outer member and an inner member defining a plurality of inner lumen, where at least one lumen can serve as a drug delivery conduit (see, e.g., FIG. 5D); or a combination of multiple inner members comprising one or multiple inner lumen (see, e.g., FIG. 5E). In the multi-lumen embodiment, one of the lumen can define a space through which a guidewire or support member is threaded to facilitate positioning of the catheter.

Figure 6:
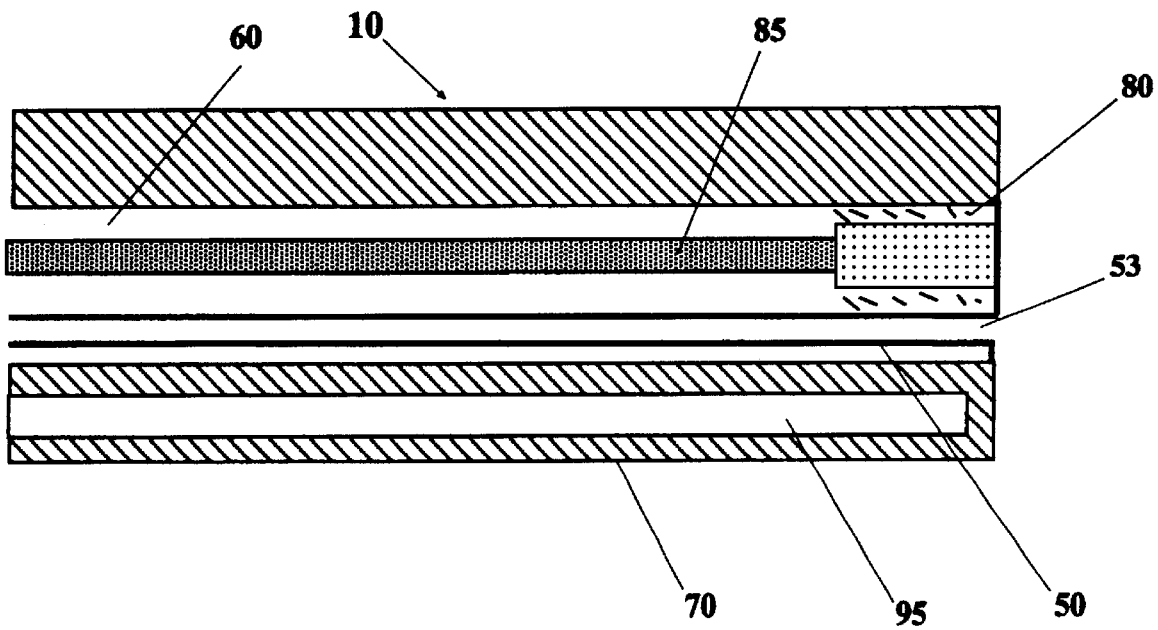
FIG. 6 is a cut-away view of a composite catheter of the invention comprising a lumen having a closed distal end.

In one embodiment, a lumen having a closed distal end 59 is defined by the catheter (e.g., the catheter outer member or by a relatively large catheter inner member) to provide for slideable insertion of a pushing element (e.g., a mandrel) to facilitate implantation of the catheter (see, e.g., FIG. 6). In this embodiment, the pushing element is inserted into the catheter, and used to position the catheter within the subject's body during implantation. Once the catheter is positioned where desired, the pushing element is withdrawn. The empty lumen can then be filled with a material (e.g., liquid, solid, or semi-solid), which material preferably comprises an antimicrobial agent (e.g., bacteriostatic or bactericidal agent).

Composite Catheter Comprising a Distal Extension

In specific embodiments of the invention, the catheter comprises a distal extension, which is positioned adjacent the distal end of the inner member. Preferably the distal extension is floppy (i.e., flexible, e.g., has a low flexural modulus relative to the flexural modulus of the body of the catheter comprising both the inner and outer members, or relative to the flexural modulus of the inner member). Where the distal extension is floppy, this portion may be referred to herein as a floppy distal extension or floppy distal portion. The flexibility of the floppy distal extension facilitates the catheter's negotiation of curves and tortuous bends (e.g., in vessels, ducts, or arteries) during implantation, and further reduces the risk of damage to the surrounding tissue. The catheter distal extension can be of any desired length, generally from about 1 cm to about 20 cm, usually from about 2 cm to about 10 cm.

The distal extension of the catheter can be provided in any of a variety of configurations. For example, the distal extension can be an extension of the distal end of the outer member beyond the distal end of the inner member. The extension of the outer member can comprise the same or different materials as the body of the outer member. Alternatively, the distal extension can be provided as an additional element that can be permanently attached to the catheter distal end.

One exemplary embodiment of a composite catheter having a floppy distal extension is illustrated in FIGS. 7 and 9. In this embodiment, the catheter 10 comprises a floppy distal extension 18, which portion is primarily composed of an extension of the distal end of the outer member 70, and comprises a thicker wall over a substantial part of its length. The extended distal end of the outer member 70 is composed of a material that provides for the desired flexibility of the catheter floppy distal extension 18, which material may be the same or different from the material of the remaining portion of the outer member. In the embodiment illustrated in FIG. 7A, the distal extension of the outer member defines a lumen 74 that extends from the distal end of the inner member lumen 53 (e.g., at the point where the inner member 50 terminates within the outer member 70) to the distal end of the catheter 10, and communicates with the inner lumen 53 of inner member 50. The drug delivery conduit 90 is thus composed of both the inner member lumen 53 (from the proximal catheter end to the distal end of the inner member) and the lumen 74 of the extended outer member distal extension 74 (from the distal end of the inner member to the distal end of the catheter) and facilitates flow of drug (indicated by arrow 93) out a drug delivery outlet 91 at the catheter distal end 12. The distal extension 18 of the catheter 10 in this embodiment is floppy (flexible), thus facilitating placement of the catheter at a treatment site, anchoring at the treatment site, and/or adjustment of the catheter length prior to implanting (e.g., by cutting the catheter's floppy distal end to length).

The drug delivery conduit of the exemplary catheter of FIG. 7A can extend to the extreme catheter distal end 12 to define a single drug delivery outlet 91. Alternatively or in addition, the distal extension can comprise a plurality of drug delivery outlets 91, which can be defined by the wall of the distal extension 18 (see, e.g., FIG. 7C). Alternatively, or in addition, the drug delivery outlet 97 can be defined by one or more slits in the wall of the catheter distal extension 18 (see, e.g., FIG. 7B) In use, the distal extension 18 is positioned within or adjacent a treatment site, and drug is delivered through the drug delivery conduit and out the drug delivery outlet(s). Use of this embodiment of the catheter of the invention for delivery of drug to the central nervous system (e.g., to the spine 5 for intraspinal delivery) is exemplified in FIG. 8.

In another embodiment, drug delivery conduit terminates at a point prior to the proximal end of the catheter distal extension. As exemplified in FIG. 9, drug delivery conduit 91 exits out a side of the catheter 10, which may be accomplished by providing an exit through both a side wall of the inner member 50 and outer member 70, or by orienting the distal end 52 of the inner member 50 toward an opening defined in a wall of the outer member 70 (see, e.g., FIG. 10). The distal extension 18 of catheter 10 may be substantially solid, or may be substantially hollow with a barrier wall 20 positioned at a point near or at the distal end of the distal extension 18. In contrast to the embodiment above, the drug delivery conduit 90 is defined substantially only by the inner member lumen. This embodiment of the catheter thus maintains the smaller inner lumen defined by the inner member for the entire drug delivery conduit, and provides for shorter drug residence time in the catheter. In use, drug is delivered from the catheter at a point just proximal to the beginning of the distal extension(see, e.g., FIG. 11, which illustrates use of the catheter in delivery of drug to the central nervous system (e.g., to the spine 5 for intraspinal delivery)).

Drug Delivery Devices Suitable for Use with the Composite Catheter of the Invention The catheter of the invention can be provided in connection with a drug delivery device. In this embodiment, it may be desirable to include a component that facilitates attachment of the catheter to the drug delivery device and/or stabilize such attachment, e.g., substantially diminish movement of the catheter in a direction perpendicular to the longitudinal axis of the drug delivery device (e.g., to provide strain relief), so as to reduce risk of breakage of the catheter at the attachment site. As exemplified in, for example, FIGS. 7 and 9, the drug delivery device 100 minimally comprises a controlled drug release device, such as an osmotic pump, having a proximal end and a distal end, which distal end defines a drug delivery orifice. The drug delivery orifice provides a drug flow pathway from a drug reservoir within the drug delivery device, and may be provided as a distinct opening or as a series of openings, e.g., as in the context of a rate-limiting membrane, which membrane defines a plurality of openings through which drug may flow from the drug reservoir. The distal end of the drug delivery device is attached to a proximal end 11 of the catheter so that the drug flow pathway from the drug delivery device reservoir continues through the drug delivery device orifice and into the drug delivery conduit 90 of the catheter 10. The catheter 10 thus communicates with the drug delivery device in a manner that facilitates movement of drug from the drug delivery device 100, through the catheter 10, and out the drug delivery outlet 91 of the catheter 10.

In general, drug delivery devices suitable for use with the catheter of the present invention are those devices that can provide for delivery of the drug from a drug reservoir at a selected or otherwise patterned amount and/or rate, preferably at a low volume rate. In general, depending on the concentration of drug, the amount of drug delivered can range from about 0.01 $\mu$g/day to about 100 mg/day. Controlled release of drug can be accomplished in any of a variety of ways according to methods well known in the art, e.g., by incorporation of drug into a polymer that provides for substantially controlled diffusion of drug from within the polymer, by incorporation of drug in a biodegradable polymer, by providing any of a variety of pumping mechanisms (e.g., an osmotically-driven device), etc. Drug can be delivered through the catheter to the treatment site as a result of capillary action, as a result of pressure and fluid flow generated from the drug delivery device, or by diffusion through the device and/or the catheter.

The drug reservoir of the drug delivery device is preferably made of an impermeable material that is sufficiently strong to ensure that it will not leak, crack, break or distort so as to expel its active agent contents under stresses it would be subjected to during use, e.g., due to physical forces exerted upon the controlled drug release device as a result of movement by the subject or physical forces associated with pressure generated within the reservoir associated with drug delivery through the catheter. The drug reservoir must also be chemically inert (e.g., does not react with the active agent formulation) and is preferably biocompatible (e.g., is non-reactive with respect to a subject's body or body fluids).

Controlled drug release devices suitable for use in the drug delivery devices of the invention may be based on any of a variety of drug delivery systems. For example, the controlled drug release device can be based upon a diffusion-based delivery system, e.g., erosion-based delivery systems (e.g., polymer-impregnated with drug placed within a drug-impermeable reservoir in communication with the drug delivery conduit of the catheter of the invention), electrodiffusion systems, and the like. In other embodiments, the controlled drug release device is based upon a convective drug delivery system, e.g., systems based upon electroosmosis, vapor pressure pumps, electrolytic pumps, effervescent pumps, piezoelectric pumps, osmotic pumps, etc.

Controlled drug release devices based upon a mechanical or electromechanical infusion pump, may also be suitable for use with the present invention. Examples of such devices include those described in, for example, U.S. Pat. Nos. 4,692,147; 4,360,019; 4,487,603; 4,360,019; 4,725,852, and the like. In general, the present invention can be used in conjunction with refillable, non-exchangeable pump systems that are normally used to deliver a substance through a relatively impermeable catheter. In this latter context the present invention provides several advantages, including improved and repeated access to a treatment site, as well as the elimination of fluid coupling issues normally associated with the conventional use of such devices.

In a preferred embodiment, the controlled drug release device is an osmotically-driven device. Exemplary osmotically-driven devices suitable for use in the invention include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like.

In a preferred embodiment, the controlled drug release device is an osmotic pump, more preferably an osmotic pump similar to that described in U.S. Pat. No. 5,728,396. In a particularly preferred embodiment, the osmotic pump is a DUROS™ osmotic pump. In general, osmotic pumps operate by imbibing fluid from the outside environment and releasing corresponding amounts of the therapeutic agent. The reservoirs of osmotic pumps can be a single chamber, or can be divided into two chambers (e.g., a piston can separate the two chambers). Where the pump comprises two chambers, the first chamber (which lies within one portion of the controlled drug release device reservoir) contains a fluid-imbibing agent, and the second chamber (which lies within a second portion of the controlled drug release device reservoir) contains a therapeutic agent. The fluid-imbibing agent in the first chamber is isolated from the active agent in the second chamber. Where a piston serves to separate the two chambers, the piston is capable of sealably moving under pressure within the reservoir.

Although controlled release of drug is described above as being primarily attributed to characteristics of the drug delivery device (e.g., the type of controlled drug release device incorporated into the drug delivery device), other aspects, features, or embodiments of the invention can facilitate controlled release of drug, and are within the scope of and contemplated by the present invention. For example, characteristics of the catheter (e.g., dimensions of the drug delivery conduit, particularly the inner diameter of the inner member defining at least a portion of the drug delivery conduit) can facilitate or further facilitate controlled release of drug from a drug reservoir to the treatment site. In another example, the catheter can be loaded with polymer that provides for controlled diffusion of drug from the drug reservoir.

Drugs for Delivery Using the Drug Delivery System of the Invention

Any of a wide variety of drugs can be delivered using the drug delivery system of the invention. Drugs suitable for delivery are preferably provided as flowable formulations, and are generally provided as liquids or semisolids. The drugs may be anhydrous or aqueous solutions, suspensions or complexes, and may be formulated with pharmaceutically acceptable vehicles or carriers, as well as additional inert or active ingredients. The drugs of formulations suitable for delivery using the invention may be in various forms, such as uncharged molecules, components of molecular complexes or pharmacologically acceptable salts. Also, simple derivatives of the agents (such as prodrugs, ethers, esters, amides, etc.) that are easily hydrolyzed by body pH, enzymes, etc., can be employed. Preferably the agents are formulated so as to remain stable for long periods of storage on the shelf or under refrigeration, as well as for long periods stored in an implanted drug delivery system of the invention.

Of particular interest is the treatment of diseases or conditions that require long-term therapy, e.g., chronic and/or persistent diseases or conditions for which therapy involves treatment over a period of several days (e.g., about 3 days to 10 days), to several weeks (e.g., about 3 or 4 weeks to 6 weeks), to several months or years, up to including the remaining lifetime of the subject. Subjects who are not presently suffering from a disease or condition, but who are susceptible to such may also benefit from prophylactic therapies using the devices and methods of the invention.

Attachment of a Drug Delivery Device to a Catheter of the Invention

Figure 12:
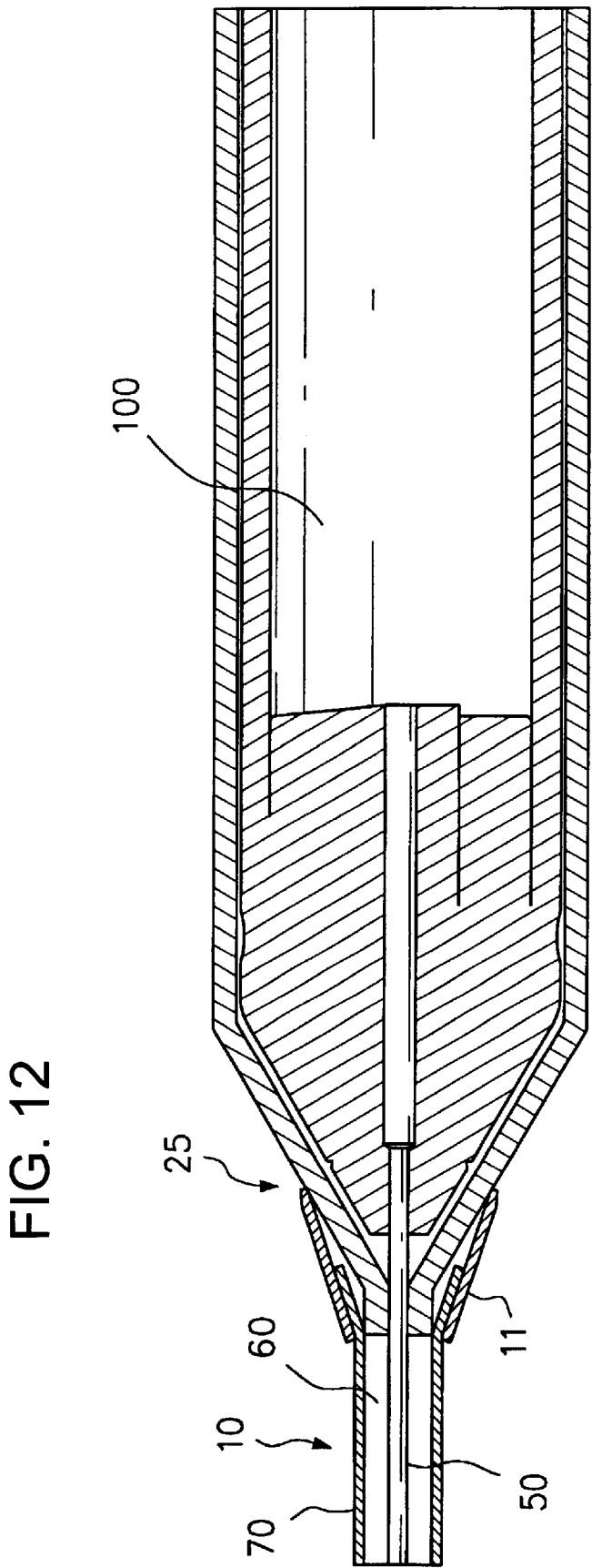
FIG. 12 is a cut-away view of a composite catheter of the invention comprising an attachment element and attached for use with a drug delivery device.

The catheter of the invention can be modified to be permanently fixed to a drug delivery device (e.g., the catheter can be an extension of a drug delivery device component (e.g., outer sheath of a drug delivery device) or can be attached by welding, adhesive bonding, etc.). Alternatively, the catheter of the invention can comprise an attachment element 25 for attaching the catheter to a drug delivery device (see, e.g., FIGS. 7, 9, and 12). The attachment element 25 facilitates and maintains a connection between a drug delivery device and a catheter of the invention, and thus maintains a drug flow pathway from a drug reservoir of a delivery device to a treatment site, during use in drug delivery to a treatment site. Such an attachment element may provide for permanent or reversible attachment of the drug delivery device to the catheter, and preferably provides for a leak-proof seal between the catheter and the drug delivery device.

Any of a variety of attachment elements are compatible for use in the drug delivery system of the invention. The attachment element can be provided as a portion of or component associated with the catheter proximal end, the drug delivery device distal end, or a combination of both. The attachment element can be fashioned from or attached to a proximal portion of the catheter outer member, which proximal portion is extended beyond the proximal end of the catheter inner member. For example, the attachment element can be a press fit lock fashioned from or attached to a portion of such an extended catheter outer member. In another example, the attachment element is a combination of a threaded connector elements, luer lock elements, bayonet connectors, etc. Alternatively, the attachment element can be provided by a catheter receiving element positioned at the distal end of the drug delivery device, e.g., the proximal end of the catheter can permanently or removably inserted into the body of the drug delivery device. In this latter embodiment, the proximal end of the catheter may not require any additional elements to accomplish attachment to the drug delivery device.

Use of the Catheter of the Invention in Drug Delivery

The catheter of the invention can be used in a wide variety of subjects. For example, the catheter can be implanted with an associated drug delivery device at any convenient site within the subject's body and oriented for delivery to any desired treatment site. In one embodiment, the catheter and the associated drug delivery device are partially or completely implanted, with at least portion of the drug delivery device retained at an accessible, external or subcutaneous site within the subject's body (e.g., under the skin of the arm, shoulder, neck, back, or leg) or within a body cavity (e.g., within the mouth). The site of implantation can be at a site close (e.g., within a few centimeters, e.g., within about 2 cm), or at a site relatively distant (e.g., more than about 30 cm, generally greater than about 50 cm to 100 cm) from the treatment site, and thus the ultimate site of drug delivery. A single catheter and/or drug delivery device, or two or more catheters and/or drug delivery devices can be implanted in a subject during the course of a therapeutic program.

In one embodiment, the catheter is primed with drug prior to implantation, e.g., the drug delivery conduit is substantially pre-filled with drug. Priming of the catheter reduces delivery start-up time, i.e., time related to movement of the drug from the drug delivery device to the distal end of the catheter. This feature is particularly advantageous where the drug delivery device releases drug at or below a low or very low volume rate (e.g., 0.4 μl/day). The drug used to prime the catheter may be the same drug that is delivered from the drug delivery device, or may be a different drug or different formulation of the drug, e.g., the catheter itself may provide for a component of the therapeutic regimen.

The catheter can be designed for temporary use, or to remain implanted in the subject for an extended period, e.g., from several days, to several weeks or months, and can be designed to be substantially permanently implanted in the subject (e.g., for the subject's remaining lifespan). The drug delivery devices can be removably attached to the catheter, or may be permanently affixed. Where the drug delivery device is removably attached, the drug delivery device can be removed following a desired drug administration period, and, where desirable replaced with a similar or different drug delivery device.

The devices of the present invention (e.g., catheter, drug delivery device, drug delivery system comprising a drug delivery device and catheter) are preferably rendered sterile prior to use. This may be accomplished by separately sterilizing each component, e.g., by gamma radiation, steam sterilization or sterile filtration, etc., then aseptically assembling the final system. Alternatively, the devices may be assembled, then terminally sterilized using any appropriate method.

Insertion of the catheter and/or drug delivery device can be accomplished using methods and tools that are well known in the art. Insertion of the catheter is generally accomplished in a manner similar to insertion of any of a variety of catheters, e.g., under aseptic conditions with at least some local or general anesthesia administered to the subject. Where the catheter comprises radiopaque material, insertion of the catheter can be monitored by X-ray or other means of visualization of the insertion process. Where desired, the drug delivery device and/or catheter can be anchored within the subject by any suitable conventional means. For example, sutures can be used to secure a proximal end of the drug delivery device and/or catheter at or near an implantation site. Following implantation, the catheter defines a drug delivery conduit that provides for transport of drug from a proximal catheter end to a distal catheter end, where the catheter proximal end is preferably maintained at the initial access site or implantation site and the catheter distal end is positioned so a drug delivery outlet of the catheter is positioned at, within, or adjacent the desired treatment site.

The catheter (or complete drug delivery device/catheter assembly) can be implanted for delivery of drug to a desired treatment site, the drug delivery device coupled to the catheter (e.g., where the drug delivery device is removably attached to the catheter), and, optionally, the drug delivery device and any remaining portion of the catheter completely implanted in the subject. The drug delivery device, and generally at least a portion of the catheter, are retained at an access site as described above.

The drug delivery device can be removed from the subject by locating the drug delivery device, e.g., by fingertip palpation of the subcutaneous implantation or access site. After anesthetizing the subject at least locally, an incision is made through the skin and any fibrous capsule tissue surrounding the area of implantation. The end of the device opposite the incision is pushed so that the proximal end of the drug delivery device is urged out of the incision. The drug delivery device can then be released from the catheter and withdrawn, or the entire drug delivery system (drug delivery device with catheter) withdrawn. Where the drug delivery device is released from the catheter, a replacement drug delivery device, which device may comprise the same or different drug and drug formulation, can then be attached to the catheter, and re-implanted substantially without withdrawing the catheter from the treatment site. The drug delivery device and/or catheter can be optionally anchored, e.g., by suturing a proximal end of the catheter or a portion of the drug delivery device in place at the access site. This procedure can be designed so that removal and replacement of drug delivery devices can be performed on an outpatient basis, and with minimal discomfort to the subject.

The invention as shown and described is considered to be the one of the most practical and preferred embodiments. It is recognized, however, that the departures may be made therefrom which are within the scope of the invention and that obvious modifications will occur to one skilled in the art upon reading this disclosure.

What is claimed is:

1. A composite catheter comprising:
    an outer member comprising a proximal end, a distal end, and an outer member body defining an outer member lumen, wherein the outer member body comprises a substantially biocompatible material selected from the group consisting of silicone, polyethylene, an ethylene vinyl acetate copolymer, a polyvinylchloride, polymethylmethacrylate, polyethylmethacrylate, polymethacrylate, ethylene glycol dimethacrylate, ethylene dimethacrylate, hydroxymethyl methacrylate, polyurethane, polyvinylpyrrolidone, 2-pyrrolidone, polyacrylonitrile butadiene, a polycarbonate, polyamides, a fluoropolymers, a polystyrene, a styrene acrylonitrile homopolymer, a styrene acrylonitrile copolymer, cellulose acetate, an acrylonitrile butadiene styrene homopolymer, acrylonitrile butadiene styrene copolymer, polyvinylchloride, silicone rubber, polymethylpentene, a polysulfone, a polyester, a polyimide, polyisobutylene, polymethylstyrene, a polyvinyl chloride elastomer, a polyolefin homopolymeric elastomer, a polyolefine copolymeric elastomer, a urethane-based elastomer, a natural rubber, and a synthetic rubber; and
    an inner member comprising a proximal end, a distal end, and an inner member body defining an inner member lumen, wherein the inner member is interposed within the outer member lumen so as to define an interstitial space between the inner member and the outer member, and wherein the inner member lumen defines a drug delivery conduit suitable for delivery of a drug from the inner member proximal end to the inner member distal end.

2. The composite catheter of claim 1, wherein the inner member defines at least two drug delivery conduits.

3. The composite catheter of claim 1, wherein the catheter comprises at least two inner members.

4. The composite catheter of claim 1, wherein the interstitial space comprises an antimicrobial agent.

5. The composite catheter of claim 1, wherein the catheter further comprises an distal extension at a distal end of the catheter.

6. The composite catheter of claim 5, wherein the distal extension is flexible relative to a proximal portion of the catheter.

7. The composite catheter of claim 5, wherein the distal extension is an extension of the outer member distal end.

8. The composite catheter of claim 5, wherein the distal extension is substantially hollow, and wherein the inner member lumen and a lumen defined by the distal extension form a drug delivery conduit.

9. The composite catheter of claim 5, wherein the distal extension defines an opening that provides a drug delivery outlet.

10. The composite catheter of claim 5, wherein the inner member lumen terminates in a drug delivery outlet at a sidewall of the distal extension.

11. The catheter of claim 1, wherein the inner member lumen is suitable for delivery of drug at a low volume rate.

12. The catheter of claim 1, wherein the inner diameter of the inner member lumen is from about 0.001" to 0.025".

13. The catheter of claim 1, wherein the catheter has an outer diameter of from about 0.030" to 0.060".

14. The catheter of claim 1, wherein the catheter further comprises a radiopaque marker.

15. The catheter of claim 1, wherein the catheter comprises a valve at a catheter distal end.

16. The catheter of claim 1, wherein the catheter comprises an attachment element for attaching a drug delivery device to the catheter.

17. A composite catheter comprising:
an outer member comprising a proximal end, a distal end, and an outer member body defining an outer member lumen; and
an inner member comprising a proximal end, a distal end, and an inner member body defining an inner member lumen, wherein the inner member is interposed within the outer member lumen so as to define an interstitial space between the inner member and the outer member, wherein the inner member body comprises a substantially impermeable material selected from the group consisting of a polymer, metal, glass, a polyolefin, nylon, polyethylene terephthalate, urethane, a fluorenated polymer, poly(methyl)methacrylate, polyvinylidine chloride, laminous hydrophilic polymer, laminous hydrophobic polymer, acrylonitrile, nickel titanium, superelastic nickel titanium, and laminates of hydrophilic and hydrophobic polymers, and wherein the inner member lumen defines a drug delivery conduit suitable for delivery of a drug from the inner member proximal end to the inner member distal end.

18. A composite catheter comprising:
an outer member comprising a proximal end, a distal end, and an outer member body defining an outer member lumen;
an inner member comprising a proximal end, a distal end, and an inner member body defining an inner member lumen, wherein the inner member is interposed within the outer member lumen so as to define an interstitial space between the inner member and the outer member, and wherein the inner member lumen defines a drug delivery conduit suitable for delivery of a drug from the inner member proximal end to the inner member distal end; and
a support member positioned within the interstitial space, wherein the support member comprises a material selected from the group consisting of metal, a metal alloy, carbon fiber, a polycarbonate, a polymer, plexiglass, stainless steel, parylene-coated stainless steel, Teflon-coated stainless steel, and nickel titanium.

19. The composite catheter of claim 18, wherein the support member is a compression support member.

20. The composite catheter of claim 19, wherein the compression support member is slidable within the interstitial space.

21. The composite catheter of claim 18, wherein the support member is a tensile support member.

22. A drug delivery system comprising:
a composite catheter comprising:
an outer member comprising a proximal end, a distal end, and an outer member body defining an outer member lumen; and
an inner member comprising a proximal end, a distal end, and an inner member body defining an inner member lumen, wherein the inner member is interposed within the outer member lumen so as to define an interstitial space between the inner member and the outer member, and wherein the inner member lumen defines a drug delivery conduit suitable for deliver a drug from the inner member proximal end to the inner member distal end; and
a drug delivery device
wherein the drug delivery device is attached to the catheter to facilitate delivery of a drug from the drug delivery device and through the inner member lumen of the composite catheter, and wherein the drug delivery device facilitates controlled release of drug at a volume rate of from about 0.01 $\mu$l/day to about 200 $\mu$l/day.

23. The drug delivery system of claim 22, wherein the catheter is detachably attached to the drug delivery device.

24. The drug delivery system of claim 22, wherein the drug delivery device is a convective drug delivery device.

25. The drug delivery system of claim 22, wherein the drug delivery device is a diffusive drug delivery device.

26. The drug delivery system of claim 22, wherein the inner member defines at least two drug delivery conduits.

27. The drug delivery system of claim 22, wherein the catheter comprises at least two inner members.

28. The drug delivery system of claim 22 wherein the interstitial space comprises an antimicrobial agent.

29. The drug delivery system of claim 22, wherein the catheter further comprises a distal extension at a distal end of the catheter.

30. The drug delivery system of claim 29, wherein the distal extension is flexible relative to a proximal portion of the catheter.

31. The drug delivery system of claim 29, wherein the distal extension is an extension of the outer member distal end.

32. The drug delivery system of claim 29, wherein the distal extension is substantially hollow, and wherein the inner member lumen and a lumen defined by the distal extension form a drug delivery conduit.

33. The drug delivery system of claim 29, wherein the distal extension defines an opening that provides a drug delivery outlet.

34. The drug delivery system of claim 29, wherein the inner member lumen terminates in a drug delivery outlet at a sidewall of the catheter proximal to the distal extension.

35. The drug delivery system of claim 22, wherein the inner member lumen is suitable for delivery of drug at a low volume rate.

36. The drug delivery system of claim 22, wherein the inner diameter of the inner member lumen is from about 0.001" to 0.025".

37. The drug delivery system of claim 22, wherein the catheter has an outer diameter of from about 0.030" to 0.060".

38. The drug delivery system of claim 22, wherein the catheter further comprises a radiopaque marker.

39. The drug delivery system of claim 22, wherein the catheter comprises a valve at a catheter distal end.

40. The drug delivery system of claim 22, wherein the catheter comprises an attachment element for attaching the drug delivery device to the catheter.

41. The drug delivery system of claim 40, wherein the catheter is detachably attached to the drug delivery device.

42. The drug delivery system of claim 22, wherein the drug delivery device is a convective drug delivery device.

43. The drug delivery system of claim 22, wherein the drug delivery device is a diffusive drug delivery device.

* * * * *